United States Patent
Tepic et al.

[11] Patent Number: 5,151,103
[45] Date of Patent: Sep. 29, 1992

[54] POINT CONTACT BONE COMPRESSION PLATE

[75] Inventors: Slobodan Tepic, Davos; Stephen Perren, Davos Dorf; Fritz Straumann, Waldenburg; Franz Sutter, Niederdorf, all of Switzerland

[73] Assignee: Synthes (U.S.A.), Paoli, Pa.

[21] Appl. No.: 662,634

[22] Filed: Feb. 28, 1991

Related U.S. Application Data

[60] Division of Ser. No. 492,403, Mar. 8, 1990, Pat. No. 5,053,036, which is a continuation of Ser. No. 247,357, Sep. 21, 1988, abandoned.

Foreign Application Priority Data

[30] Nov. 3, 1987 [EP] European Pat. Off. .PCTEP87/00663

[51] Int. Cl.$^5$ ................................................ A61F 5/24
[52] U.S. Cl. .......................................... 606/69; 606/72
[58] Field of Search .................... 606/61, 69, 70, 72, 606/74

[56] References Cited

FOREIGN PATENT DOCUMENTS

| 0048038 | 3/1982 | European Pat. Off. .............. 606/69 |
| 2933637 | 4/1980 | Fed. Rep. of Germany ........ 606/70 |

*Primary Examiner*—David Isabella
*Assistant Examiner*—Debra S. Brittingham
*Attorney, Agent, or Firm*—Davis Hoxie Faithfull & Hapgood

[57] ABSTRACT

A bone plate for use in osteosynthesis having a plurality of contact elements extending from its lower surface so that contact between plate and bone is reduced to the minimum contact needed during attachment of the plate to a bone.

14 Claims, 10 Drawing Sheets

POINT CONTACT BONE COMPRESSION PLATE

This application is a division of our copending application Ser. No. 492,403, filed Mar. 8, 1990, now U.S. Pat. No. 5,053,036, which application is a continuation of our application Ser. No. 247,357, filed Sep. 21, 1988, and is now abandoned.

FIELD OF THE INVENTION

The invention relates to bone plates used as implants in osteosynthesis.

BACKGROUND OF THE INVENTION

In conventional treatment of bone fractures a plate is applied to a fractured bone so as to bridge the fracture. The plate is fixed to the bone by a plurality of screws. When the screws are tightened in the bone, they produce compressive stresses between the plate and the bone. Transmission of a functional load from the bone to the plate and back to the bone is achieved mostly by means of friction corresponding to the compressive stresses.

Usually the screws securing the plate to the bone engage both the near and the far wall of the bone cortex. The cortex receives its blood supply from the periosteum on its outer side and from the endosteum on the inner side. Compression of the plate and bone impedes the blood circulation of the cortex region under the plate. This is believed to increase the chances of infection, which is a major complication of operative fracture treatment.

Dead bone under the plate is in due course remodeled and revascularized. Remodeling starts at the periphery of the unperfused bone and proceeds towards the plate. Porosity within the remodelling bone persists for a long time and reduces bone strength. This situation requires keeping the plate on the bone longer than is needed for the fracture to heal. The use of long screws running first through the near cortex, then through the medullary canal, and through the far cortex may further interfere with blood supply of the fractured bone by cutting through larger blood vessels.

SUMMARY OF THE INVENTION

In accordance with the invention the noted drawbacks of conventional plates are overcome by means of a bone plate for osteosynthesis comprising an elongated body having an upper surface and a lower surface, a plurality of screw holes traversing said body between said surfaces to attach the plate to a bone and a plurality of contact elements extending from the lower surface for contacting the bone during attachment of the plate to the bone.

Use of the plate according to the invention results in reduced damage to bone, particularly damage to the intramedullary vascular system. Moreover, plates according to the invention make it possible to use short screws which can be made self-tapping, without the problems incidental to the use of long self-tapping screws. An additional advantage is that the plate design according to the invention allows for doubling the strength of the bone plate due to reduced screw hole size. Variation in strength and rigidity along the length of the bone plate according to the invention is also much less than in conventional plates. This facilitates plate adaptation to curved bone surfaces.

DESCRIPTION OF THE DRAWINGS

The invention will be disclosed more fully in connection with the accompanying drawings in which.

DETAILED DESCRIPTION

Figure 1:
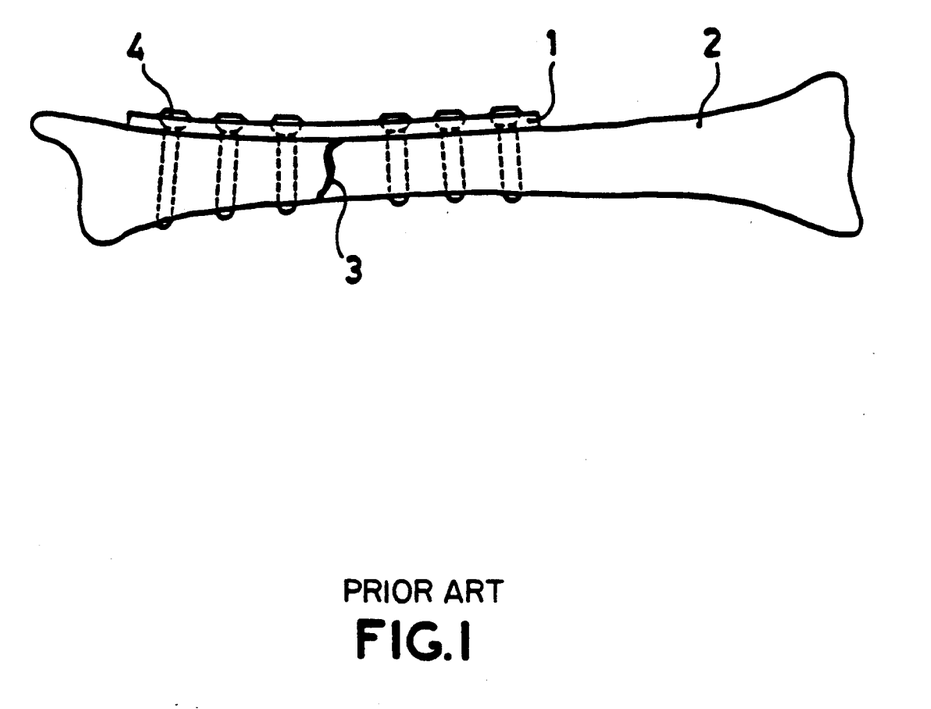
FIG. 1 is a schematic view of a fractured bone with a conventional bone plate.
Figure 2:
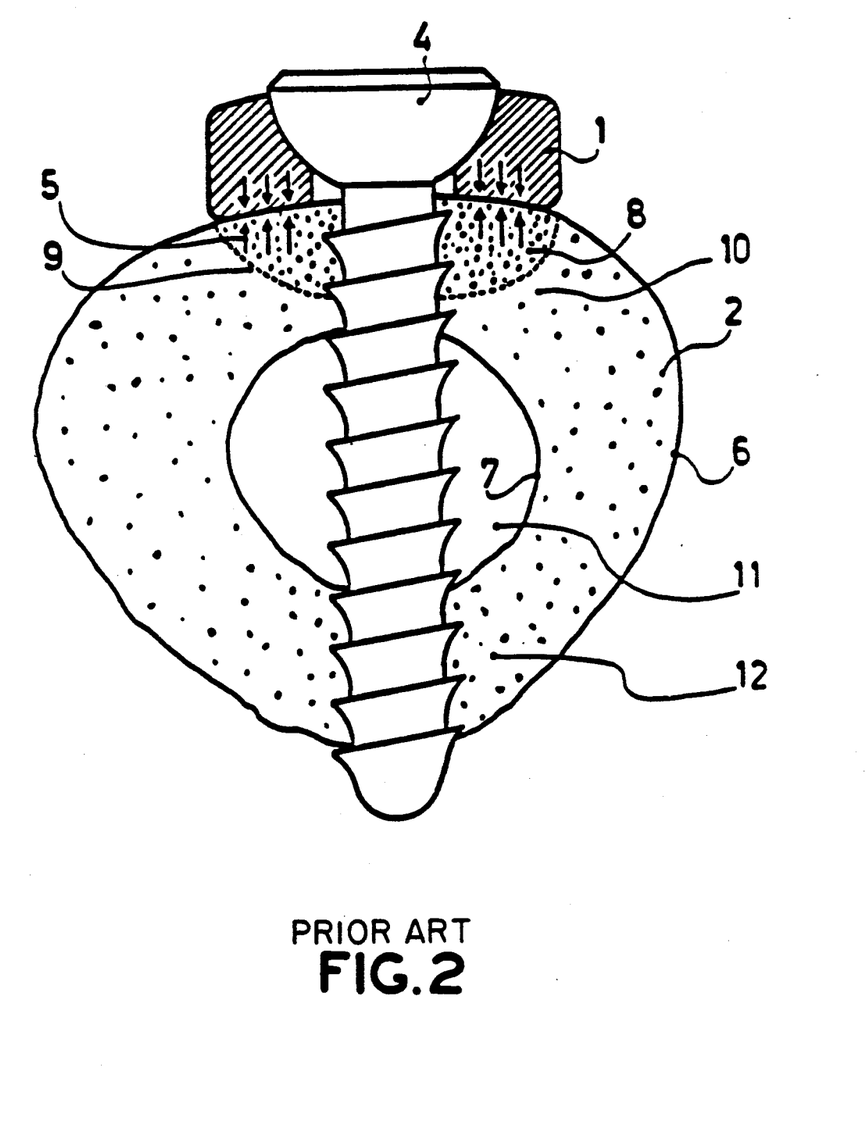
FIG. 2 is a cross-section of the bone plate of FIG. 1.

Referring to FIG. 1, a conventional bone plate 1 for the treatment of bone fractures is fixed to the bone 2 by means of a number of screws 4. Screws 4 are tightened in the bone 2 producing compressive stresses 5 (FIG. 2) between the plate 1 and the bone 2. As shown in FIG. 2, transmission of functional load from the bone 2 to the conventional plate 1 and back to the bone 2 is achieved mostly by means of friction between plate and bone corresponding to the compressive stresses 5, indicated by arrows. Both the near and far walls of the cortex of bone 2 are usually engaged by the screws 4. Bone cortex is supplied by blood from the periosteum, or outer side 6, and from the endosteum or inner side 7. Compressive stresses 5 between the conventional plate 1 and bone 2 impede the blood perfusion of the cortex region 8 under the conventional plate 1. This is believed to increase the likelihood of infection—a major complication of operative fracture treatment.

Dead bone in region 8 is in due course remodelled and revascularized. This remodelling activity starts at periphery 9 of the unperfused part of the bone and proceeds towards plate 1. Porosity within the remodelling bone persists for a long time and reduces bone strength, particularly in fatigue. It is therefore necessary to keep the conventional plate 1 on the bone for a period longer than is needed for the fracture to heal. Long screws 4, by running first through the near cortex 10, then through the medullary canal 11 and through the far cortex 12, may further interfere with blood supply to the fractured bone by cutting through larger blood vessels.

Figure 3:
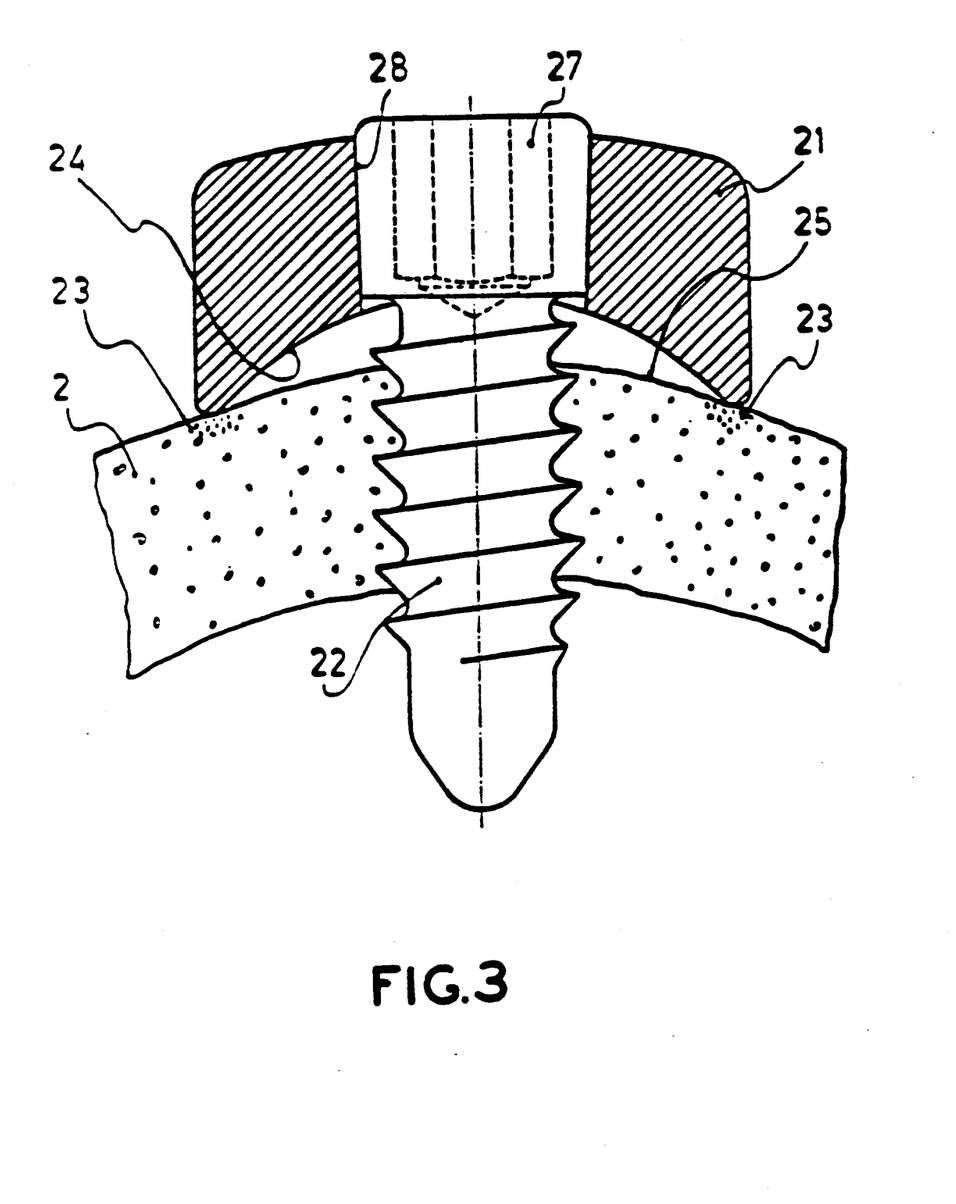
FIG. 3 is a cross-section of a bone plate according to the invention with short screws.
Figure 4:
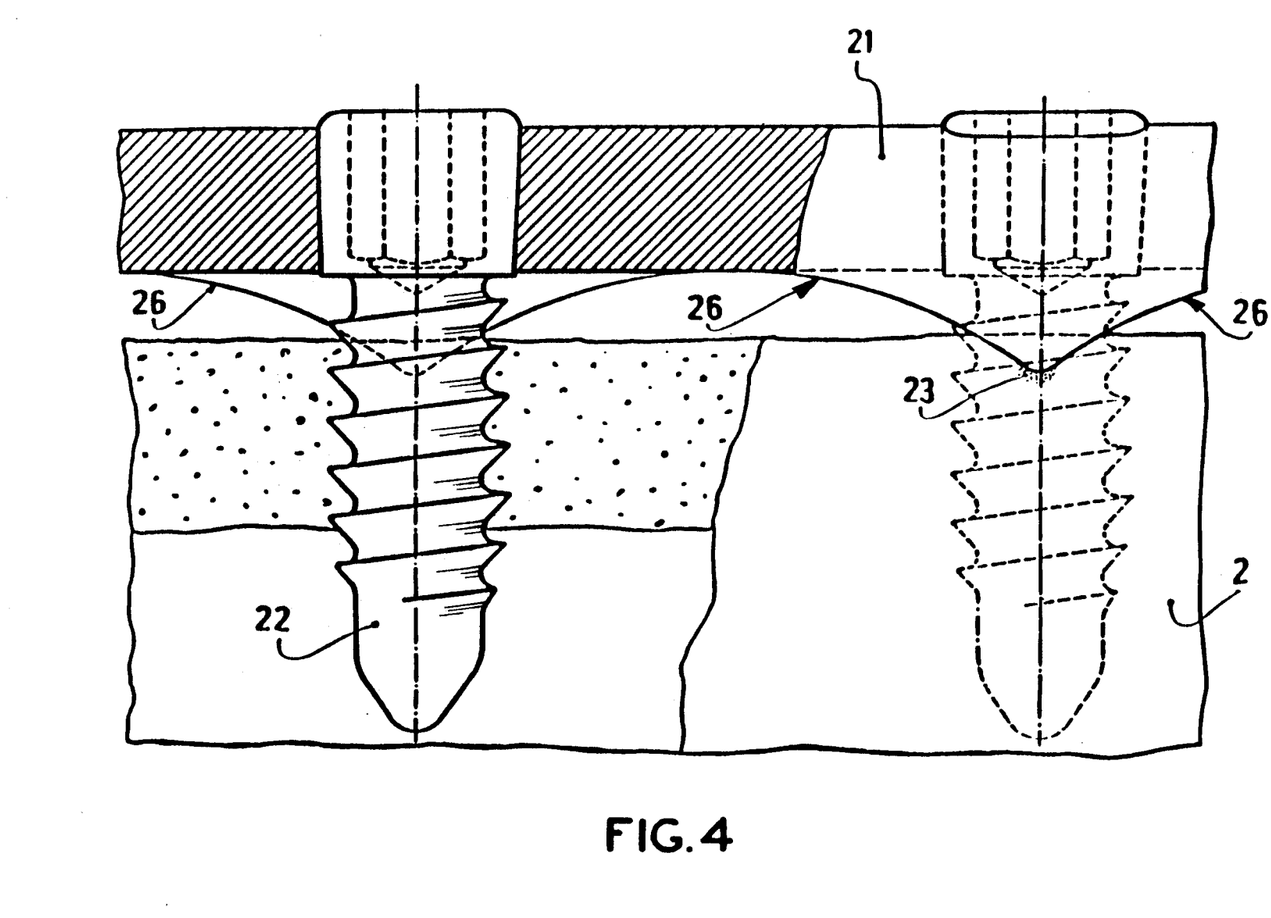
FIG. 4 is a view in side elevation and partly in vertical section of the bone plate of FIG. 3.

Referring now to FIG. 3, a plate 21 according to the invention is attached to the bone 2 by means of a plurality of short screws 22, which are inserted through conical screw holes 28 in the plate. The undersurface of the plate is shaped so as to permit contact with the bone only at points 23. In a preferred embodiment, this is achieved by arching the underside of the plate 24 at a transverse curvature of smaller radius than that of the bone's outer contour 25. In the longitudinal direction, as shown in FIG. 4, the underside of the plate is also shaped with a plurality of arches 26 between the screws 22. Therefore, the only contact between plate and bone is at points 23.

The area of contact with the bone is reduced to the minimum practicable. Preferably this is less than 5% of the total area of the lower surface of the plate and most preferably less than 2%.

As shown in FIG. 3, the plate according to the invention may be attached to the bone by a screw 22 having a conical head 27 which upon insertion locks safely in a conical hole 28 of the plate 21. The cone angle of the screw is the same as the cone angle of the screw hole. Since the angle is very small, the plate does not come loose and fall down onto the bone. In other words, the angle of the cone on the screw head 27 is smaller than the friction angle. The taper of the cone is preferably between 1:5 and 1:20.

The use of short screws 22 in place of conventional long screws is made possible because screw 22 can be locked into the plate 21. This prevents tilting of the screw 22 within the cortex of bone 2. Loads between the bone 2 and the plate 21 are transferred directly through the screws 22 which now act as pegs (under shear) rather than anchors (under tension), which would be the case if a long screw reached through the medullary canal to the far cortex. In addition to reducing damage to bone 2 and in particular to the intramedullary vascular system, short screws 22 can be made self-tapping without the problems incidental to the use of long self-tapping screws.

The undercutting of the plate 21 with arches 24 in the transverse direction and arches 26 in the longitudinal direction has advantages in addition to reducing the plate-bone contact to points 23. The strength and rigidity of conventional plates is lowest at the sections which have screw holes. Overall plate strength is limited by the weakest section. While keeping outer dimensions similar to those of a conventional plate, the plate design according to the invention allows for doubling plate strength. This is largely due to the reduced size of the screw holes. Variation of strength and rigidity along the plate is much smaller than in conventional plates. These characteristics facilitate plate adaptation to curved bone surfaces.

Figure 5:
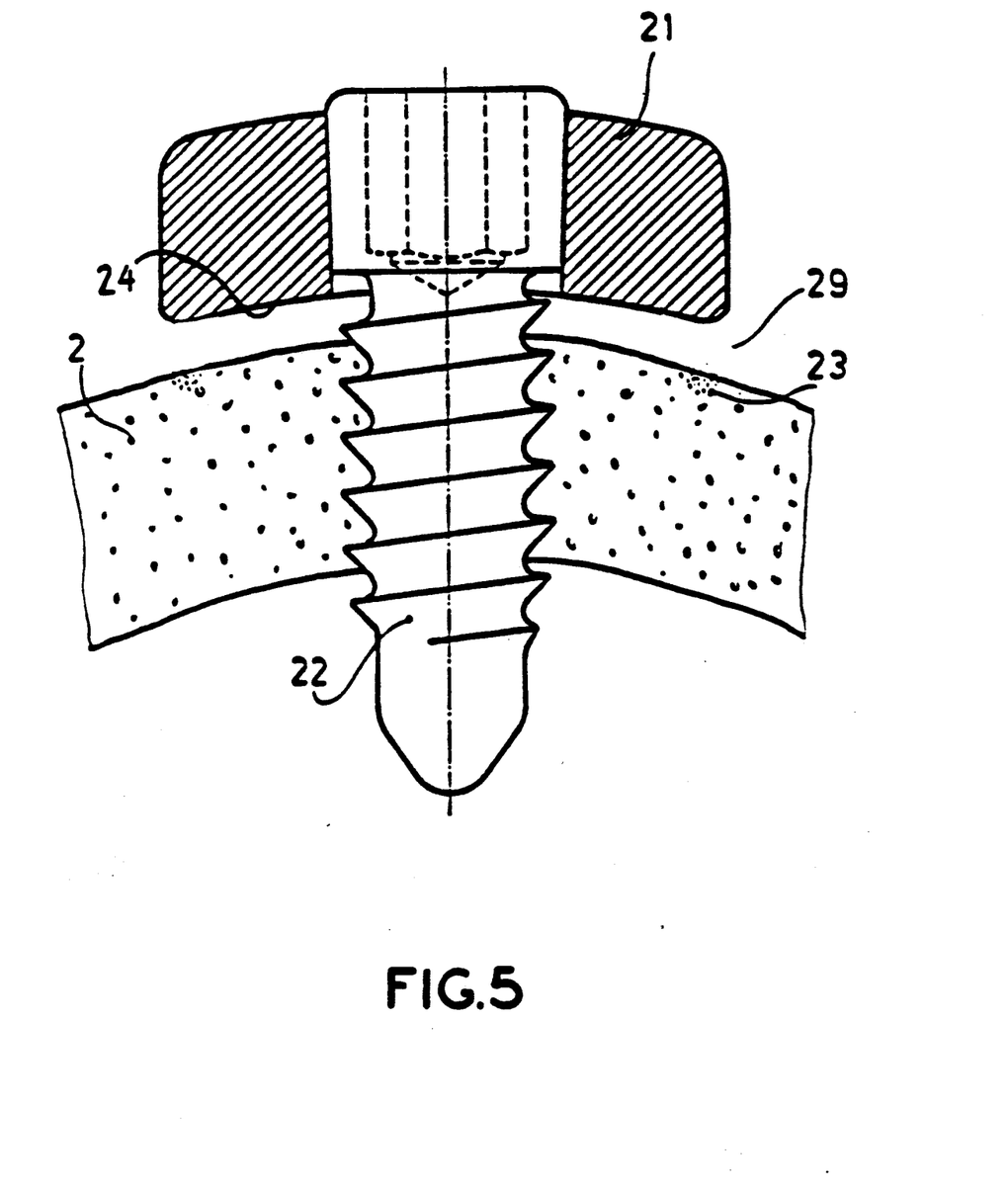
FIG. 5 is a cross-section of a bone plate according to the invention with resorbable studs at the plate undersurface.

FIG. 5 shows another embodiment of the invention in which contact between the plate 21 and the bone 22 is reduced. Small studs 29 are added to the undersurface of the plate. These studs may be made from a material which is resorbable or even dissolvable in the body (e.g. polysaccacharides), so that after the plate is positioned they will disappear entirely. This is possible because the studs are only necessary to support the plate during the procedure of inserting and locking the screw 22 into the plate 21.

Figure 6:
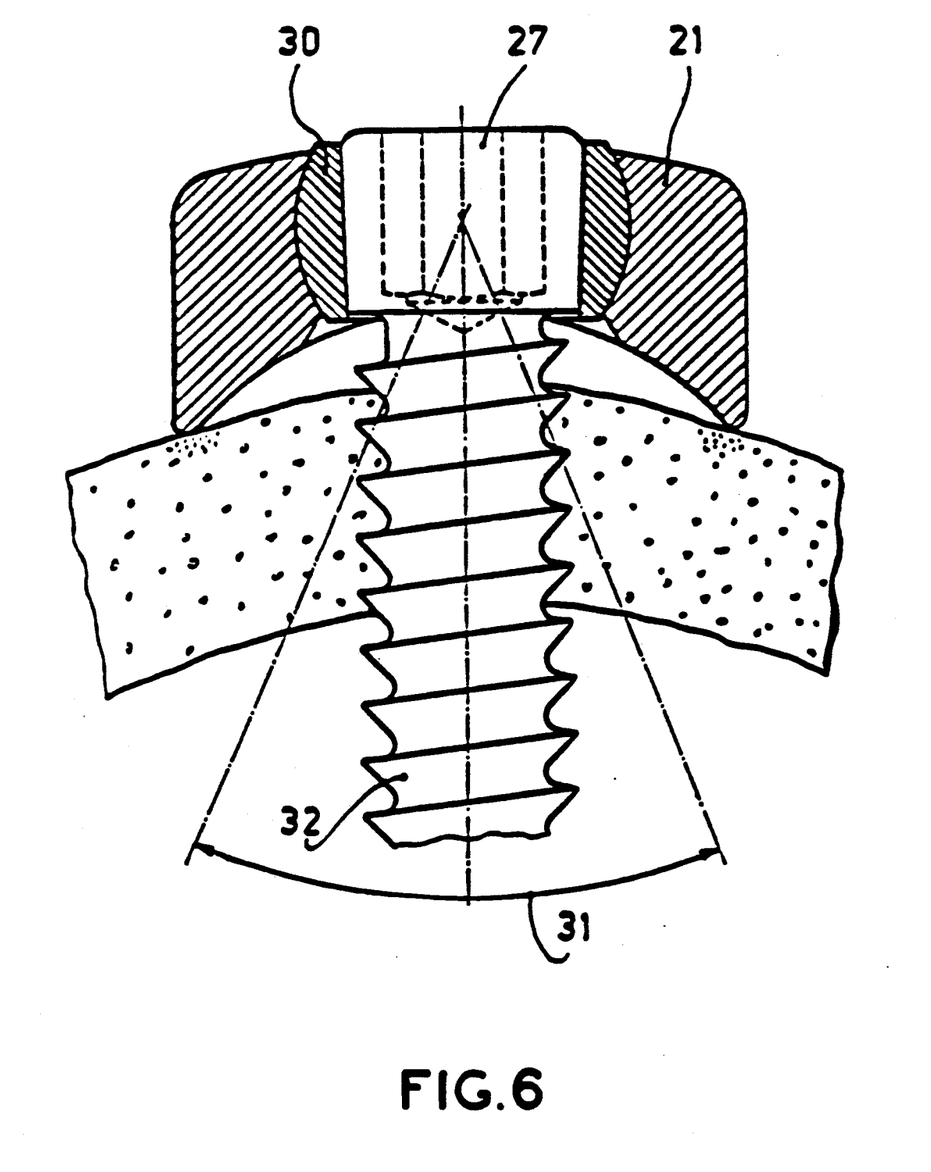
FIG. 6 is a cross-section of a bone plate according to the invention with an expandable spherical insert.
Figure 6A:
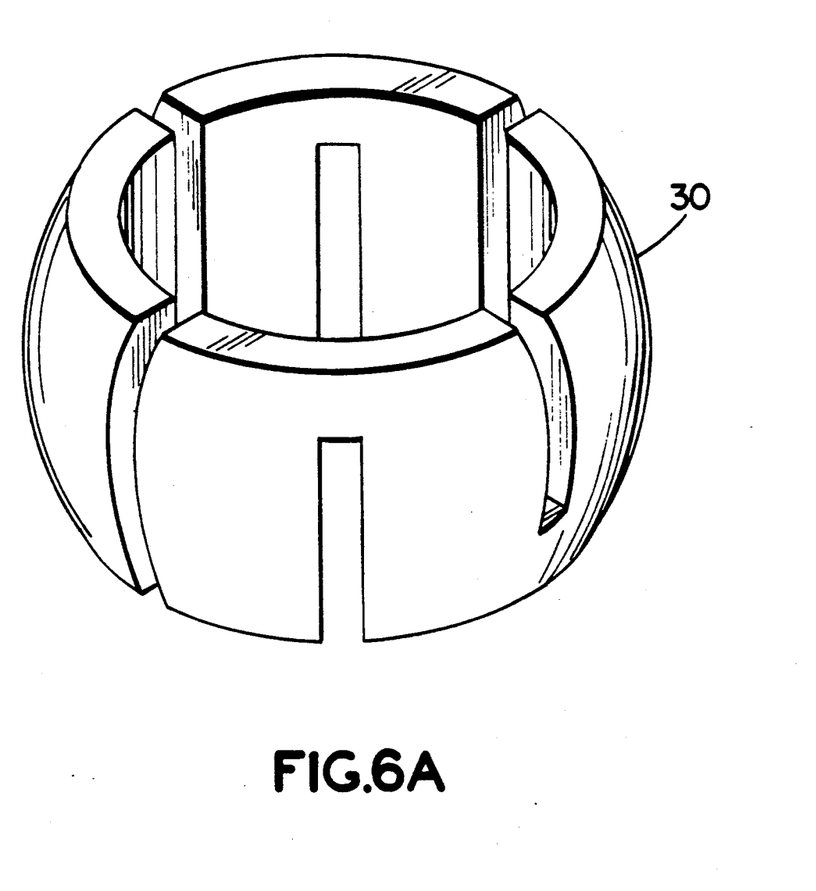
FIG. 6A is a perspective of the spherical insert of FIG. 6.

FIG. 6 shows a plate 21 according to the invention combined with a long screw 32 which may be locked into the plate 21 via a spherical insert 30. The screw is thus given substantial freedom of angular placement as indicated at 31. As it is forced into sphere 30, (see FIG. 6A) the conical head 27 of the screw 32 compresses the slotted sphere 30 against the plate, locking itself and the sphere 30 in the plate 21. The taper of the cone angle is again smaller than the friction angle, preferably between 1:5 and 1:20.

Figure 7:
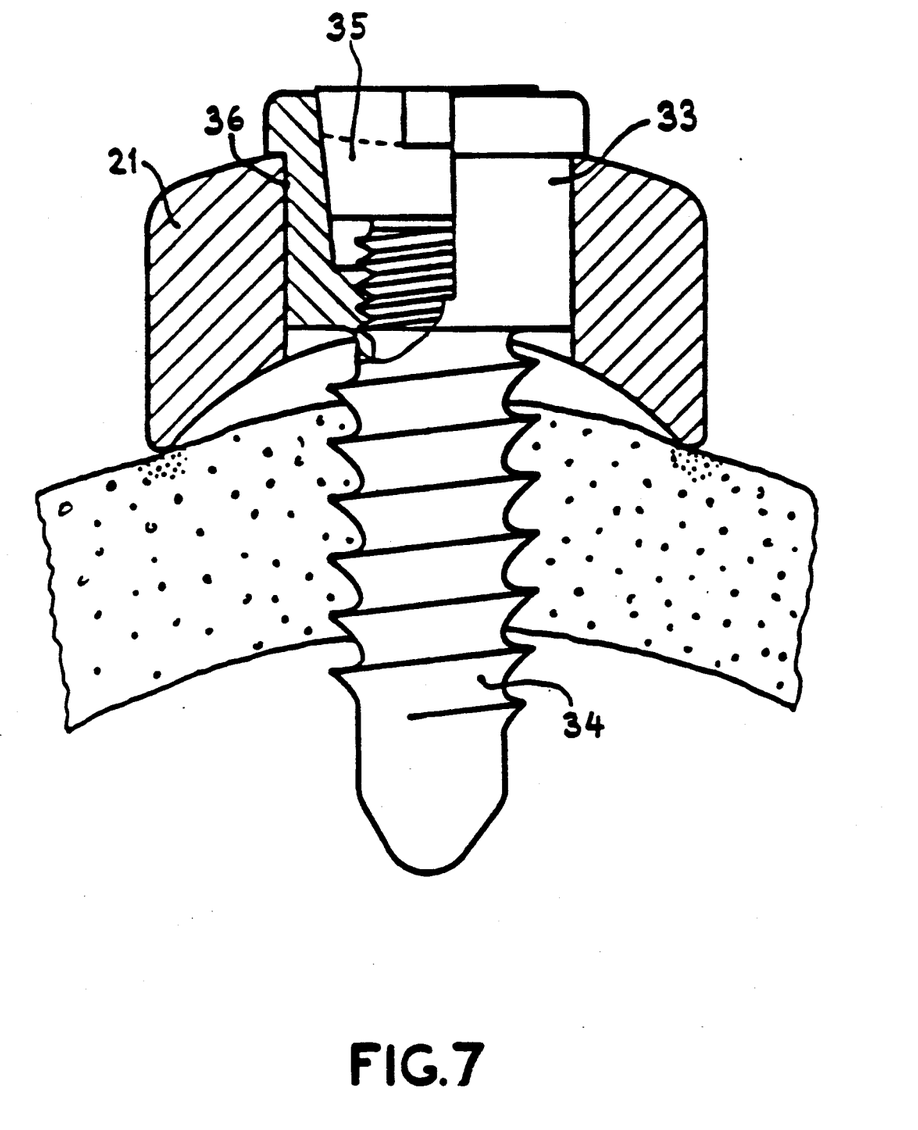
FIG. 7 is a cross-section of a bone plate according to the invention with a screw head expandable by a conical insert.

FIG. 7 shows another embodiment of the invention where the locking of the screw 34 in the plate 21 is achieved by the conical insert 35, which when driven down expands the slotted screw-head 33, thereby forming a rigid connection at the cylindrical interface 36.

Figure 8:
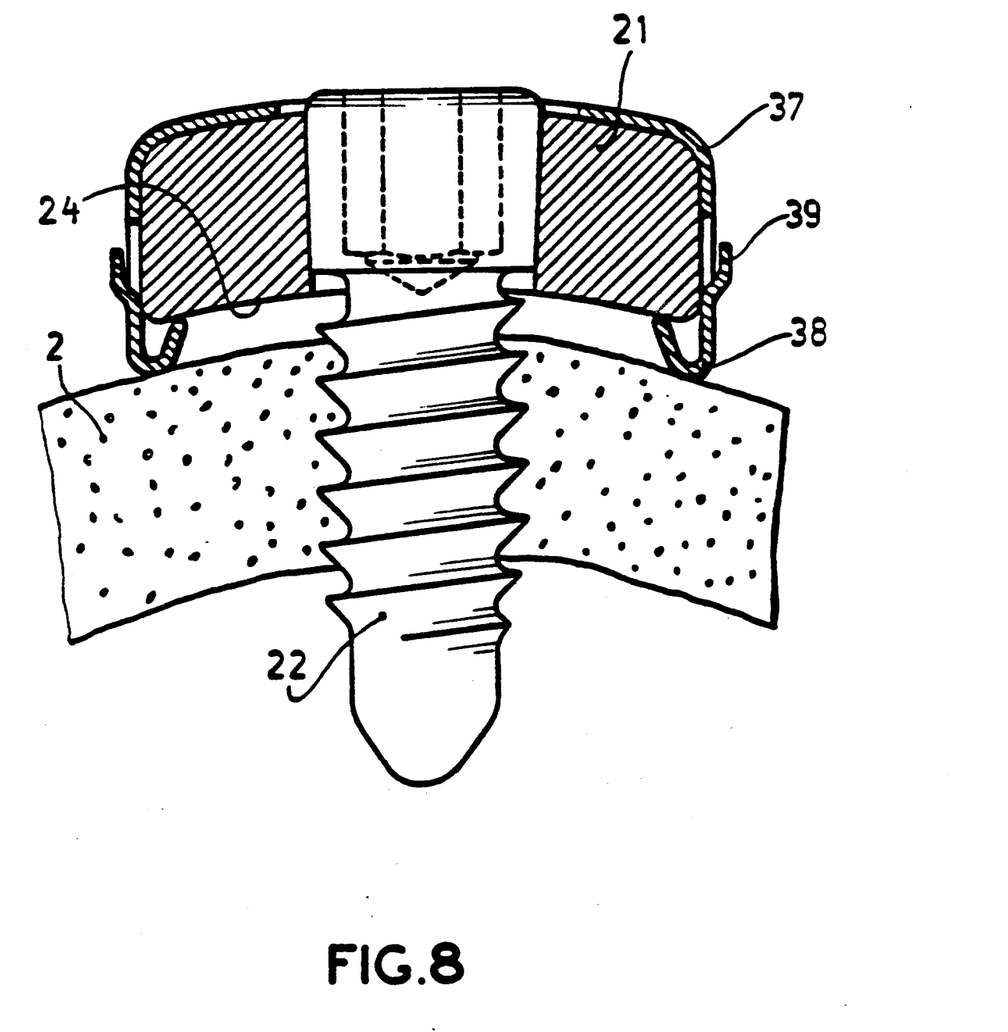
FIG. 8 is a cross-section of a bone plate according to the invention with removable clip-on springs.
Figure 9:
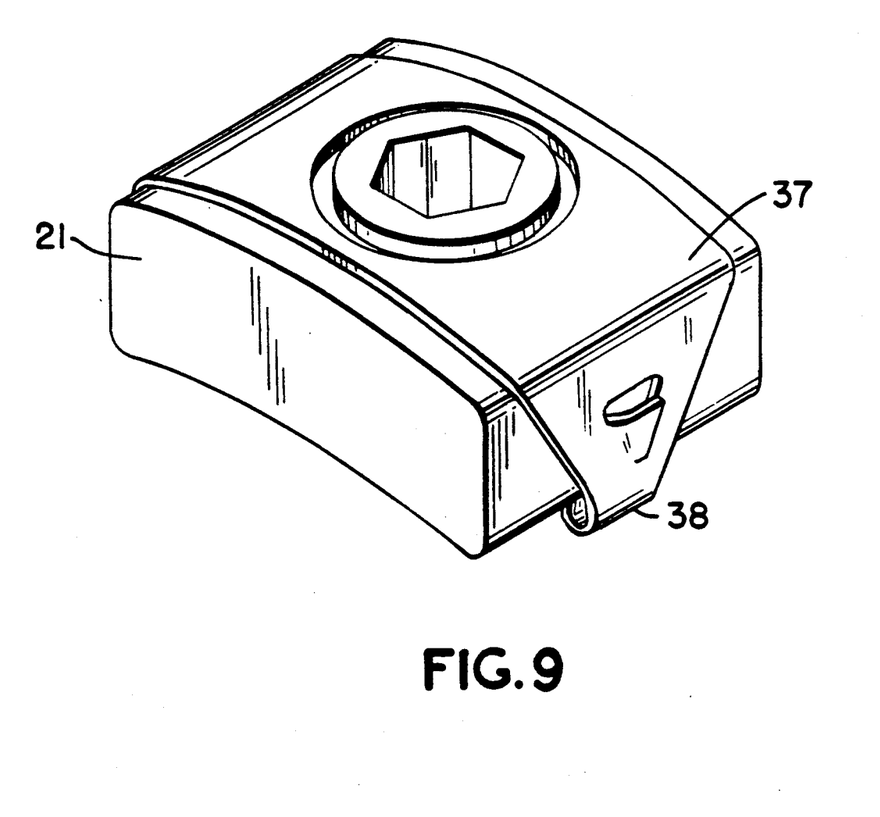
FIG. 9 is a perspective view of a section of the bone plate according to FIG. 8 showing a clip-on spring.

FIGS. 8 and 9 show a further embodiment of the invention where the reduced plate contact with the bone 2 is achieved through removable clip-on springs 37 which provide stud-like extensions 38 on the undersurface of plate 21. Springs 37 may be removed following insertion and locking of screw 22 in the plate 21. Hooks 39 facilitate removal following screw tightening.

The plate may be constructed with one or more self-compressing screw holes of the type described in U.S. Pat. No. 31,628.

What is claimed is:

1. An implant for osteosynthesis comprising a biocompatible device for attachment to a bone, and a plurality of screws for attaching the device to the bone, the heads of said screws and the device having a predetermined friction angle relative to one another, said screws having conical heads and said device having complementary conical holes for receiving said heads in surface contact therewith, the cone angle of the conical holes being less than the friction angle between the holes and the screw head, thereby locking said screws to said device to prevent said device from sliding down the screw heads.

2. The implant claimed in claim 1, wherein the cone defining the hole has a cone taper of from about 1:5 to about 1:20.

3. The implant claimed in claim 1, wherein said device includes a plurality of clearance holes, each of said clearance holes having a compressible insert, each insert having one of said conical holes.

4. The implant claimed in claim 1, wherein the screws are self-tapping.

5. The implant claimed in claim 1, wherein the length of the screws are such that they will engage only one of the cortices of the bone to which the device is applied.

6. The implant claimed in claim 1, wherein the contact of the underside of said device with said bone is at a plurality of points.

7. The implant claimed in claim 1, wherein the device has a undersurface for application to the surface of a bone to be treated, the bone contact areas of said undersurface being less than 5% of the full undersurface area.

8. The implant claimed in claim 7, wherein the bone contact area is less than 2% of the full undersurface area.

9. Implant as claimed in claim 7, wherein the bone contact areas of the undersurface consist of contact studs made of a material which resorbable or dissoluble in body fluids.

10. The implant claimed in claim 1 and comprising clip-on springs mounted on said device and forming extensions on the undersurface of said device.

11. The implant claimed in claim 1, wherein said device is a plate.

12. The implant claimed in claim 1, wherein the heads of said screws have sockets and including elements for insertion into the sockets of said screw heads to expand said screw heads.

13. The implant claimed in claim 1, wherein the device includes a self compressing screw hole.

14. The implant claimed in claim 13, wherein the device includes a self-compressing screw hole.

* * * * *